US011465952B2

(12) United States Patent
Fletcher et al.

(10) Patent No.: US 11,465,952 B2
(45) Date of Patent: Oct. 11, 2022

(54) PROCESS TO PREPARE PROPYLENE

(71) Applicant: GASOLFIN B.V., Amsterdam (NL)

(72) Inventors: Raymond Paul Fletcher, Amsterdam (NL); Elbert Arjan De Graaf, Pooler, GA (US)

(73) Assignee: GASOLFIN B.V., Amsterdam (NL)

( * ) Notice: Subject to any disclaimer, the term of this patent is extended or adjusted under 35 U.S.C. 154(b) by 0 days.

(21) Appl. No.: 17/283,655

(22) PCT Filed: Oct. 11, 2019

(86) PCT No.: PCT/EP2019/077572
§ 371 (c)(1),
(2) Date: Apr. 8, 2021

(87) PCT Pub. No.: WO2020/074693
PCT Pub. Date: Apr. 16, 2020

(65) Prior Publication Data
US 2021/0355050 A1    Nov. 18, 2021

Related U.S. Application Data

(60) Provisional application No. 62/744,288, filed on Oct. 11, 2018.

(30) Foreign Application Priority Data

Nov. 6, 2018   (NL) ..................................... 2021941

(51) Int. Cl.
*C07C 4/06*   (2006.01)
*C10G 11/05*   (2006.01)
(Continued)

(52) U.S. Cl.
CPC ................ *C07C 4/06* (2013.01); *C10G 11/05* (2013.01); *C10G 51/026* (2013.01);
(Continued)

(58) Field of Classification Search
CPC ... C07C 4/06; C07C 2523/06; C07C 2529/40; C07C 2521/04; C07C 11/06;
(Continued)

(56) References Cited

U.S. PATENT DOCUMENTS 5,026,936 A * 6/1991 Leyshon ................. C07C 11/06
585/315
5,292,976 A   3/1994 Dessau et al.
(Continued)

FOREIGN PATENT DOCUMENTS

EP        1061116 A1    12/2000

*Primary Examiner* — Philip Y Louie
*Assistant Examiner* — Jason Y Chong
(74) *Attorney, Agent, or Firm* — Nixon Peabody LLP; Ronald I. Eisenstein; Nicole D. Kling (57) ABSTRACT

The invention is directed to a process to prepare propylene from a mixture of hydrocarbons having an olefin content of between 5 and 50 wt. % and boiling for more than 90 vol. % between 35 and 280° C. or from a hydrocarbon feed comprising paraffins, naphthenics, aromatics and optionally up to 10 wt. % of olefins, by first contacting the feed with a low acidic density cracking catalyst in a fixed bed reactor, separating propylene and subsequently contacting the residue with a high acidic density cracking catalyst in a fixed bed reactor at a more elevated temperature, separating propylene and recycling the residue to first and second cracking reactors. Aromatics may be added to first and second cracking step to improve cycle length.

25 Claims, 1 Drawing Sheet

(51) Int. Cl.
*C10G 11/02* (2006.01)
*C10G 51/02* (2006.01)

(52) U.S. Cl.
CPC ...... *C07C 2523/06* (2013.01); *C07C 2529/40* (2013.01); *C10G 2400/20* (2013.01)

(58) Field of Classification Search
CPC ...... C10G 11/02; C10G 11/05; C10G 51/026; C10G 2400/20; C10G 69/04
See application file for complete search history.

(56) References Cited

U.S. PATENT DOCUMENTS

| | | | |
|---|---|---|---|
| 6,388,161 B1* | 5/2002 | Dath | C10G 11/00 585/653 |
| 2006/0108260 A1* | 5/2006 | Henry | C10G 51/02 585/653 |

* cited by examiner

Fig.1

Fig.2

PROCESS TO PREPARE PROPYLENE

CROSS-REFERENCE TO RELATED APPLICATIONS

This application is a 35 U.S.C. § 371 National Phase Entry Application of International Application No. PCT/EP2019/077572 filed Oct. 11, 2019, which designates the U.S. and claims benefit under 35 U.S.C. § 119(a) of NL Application No. 2021941 filed Nov. 6, 2018 and under 35 U.S.C. § 119(e) of U.S. Application No. 62/744,288 filed Oct. 11, 2018, the contents of which are incorporated herein by reference in their entireties.

The invention is directed to a process to prepare propylene from a mixture of hydrocarbons having an olefin content of between 5 and 50 wt. % and boiling for more than 90 vol. % between 35 and 280° C. and/or from a hydrocarbon feed comprising paraffins, naphthenics, aromatics and optionally up to 10 wt. % of olefins by contacting the feed with a cracking catalyst in a fixed bed reactor.

Propylene is for more than 50% produced by steam cracking processes. Typical feedstock is straight run naphtha as obtained when refining a crude petroleum source which typically comprises of unsaturated compounds, like paraffinic and naphthenic compounds optionally in admixture with aromatic compounds.

Propylene is also prepared in a refinery environment as a by-products of the Fluid catalytic cracking (FCC) process. Since the late nineties, some FCC units have been operating at higher severity to achieve a propylene yield of 10-12 wt percent of the fresh FCC feed. To further increase the propylene yield, different processes have been developed around the FCC configuration in a refinery and it has been reported that propylene yields up to 20 wt. % of fresh FCC feed have been achieved. One way to increase the propylene yield is to add a medium pore zeolite to the FCC catalyst as for example described in DE4114874. Various variants have been developed wherein the medium pore catalyst and the FCC catalyst contact the hydrocarbon fractions in FCC riser reactors. A disadvantage of these processes is that the medium pore zeolite catalyst will be subjected to a regeneration step together with the FCC catalyst which causes the medium pore zeolite catalyst to degenerate.

The naphtha fraction obtained in a FCC process may also be contacted in a separate process wherein the feed is contacted with a cracking catalyst in a fixed bed reactor. One such process is described in WO99/29804 which publication describes a fixed bed reactor process wherein an olefin rich feedstock is contacted with a crystalline silicate catalyst. In the examples a light cracked naphtha (LCN) was cracked using a crystalline silicate catalyst. The propylene yield was about 18 wt. % based on feed. Experiments using a ZSM-5 and using a 1-hexene feed showed the highest propylene yield of 28.8 wt. % using a ZSM-5 having a Si/Al atomic ratio of 350 (SAR=750), while experiments using ZSM-5 having a Si/Al atomic ratio of 40 and 25 (SAR=80, SAR=50) showed a lower propylene yield and more coke formation.

GB2345294 describes a process where a olefin containing $C_4$ raffinate feed is contacted with a cracking catalyst in a fixed bed reactor. The catalyst consists of ZSM-5 containing silver instead of a proton and wherein the ZSM-5 has a SAR of 300. The reaction temperature is 600° C. at a weight hourly space velocity of 47 $h^{-1}$.

A disadvantage of the prior art processes is that the yield to propylene is low and the coke formation on the catalyst is high. This results in short cycle lengths, ie times between decoking operations, in which propylene can be made in one reactor. The object of this invention is to provide a process which can prepare propylene in a high yield while the coke formation on the catalyst is kept at a rate such that an acceptable cycle length results.

Applicants now found that the following process does not have such a disadvantage. Process to prepare propylene from a mixture of hydrocarbons having an olefin content of between 5 and 50 wt. % and boiling for more than 90 vol. % between 35 and 280° C. and/or from a hydrocarbon feed comprising paraffins, naphthenics, aromatics and optionally up to 10 wt. % of olefins wherein the process comprises the following steps:

(a) feeding the mixture of hydrocarbons optionally in admixture with a recycle stream and having a temperature between 450 and 750° C. to a fixed bed reactor where the feed is contacted with a low acidic density cracking catalyst at a hydrocarbon partial pressure of below 3 bar and at a weight hourly space velocity of between 0.5 and 100 $h^{-1}$, (b) isolating propylene and optionally other low boiling compounds from the effluent of step (a) wherein a first high boiling fractions remains, (c) feeding all or part of the first high boiling fraction optionally in admixture with a recycle stream and having a temperature between 400 and 750° C. to a fixed bed reactor where the first high boiling fraction is contacted with a high acidic density cracking catalyst at a hydrocarbon partial pressure of below 3 bar and at a weight hourly space velocity of between 0.5 and 100 $h^{-1}$ and wherein the temperature of the mixture of hydrocarbons optionally in admixture with a recycle stream as fed to the reactor in step (a) is lower than the temperature of the first high boiling fraction optionally in admixture with a recycle stream as fed to the reactor in step (c), (d) isolating propylene and optionally other low boiling compounds from the effluent of step (c) wherein a second high boiling fractions remains, and (e) recycling all or part of the second high boiling fraction to step (a) and/or to step (c) as the optional recycle stream.

Applicants now found that a hydrocarbon mixture comprising paraffins or paraffins and olefins can be effectively converted to propylene and also other lower olefins in two cracking steps. In the first step (a) the olefins and naphthenes, if present, are mainly converted to propylene, other lower olefins and paraffins. This is achieved at relatively moderate reaction conditions in the presence of a low acidic density cracking catalyst. At these conditions coke formation is minimized. The first high boiling fraction will have a higher paraffin content than the olefin hydrocarbon feed described above. This makes it possible to crack this feed at more severe conditions by contacting with a high acidic density cracking catalyst. Thus, a process is provided which can convert both the olefins and the paraffins, and even the $C_5$ paraffins, in the hydrocarbon mixture with a high yield to propylene. Further the applicants found that the coke formation can be kept low. It is believed that this is a result of the fact that the first high boiling fraction contains almost no olefins or at least a small content. Further advantages will be described below.

The feed used in step (a) is a mixture of hydrocarbons. The mixture will comprise of paraffins optionally in admixture with aromatics, naphthenic compounds and olefins having an olefin content of between 5 and 50 wt. % and boiling for more than 90 vol. % between 35 and 280° C. and preferably for more than 90 vol. % between 35 and 240° C. The mixture of hydrocarbons will suitably comprise paraffins, naphthenic and/or aromatics next to the olefins. Such mixtures may be obtained from any source. Suitably the mixture of hydrocarbons comprises or is a fraction as isolated from the effluent of a Fluid Catalytic Cracking process such as light cat cracked naphtha, medium cat cracked naphtha, heavy cat cracked naphtha. Other examples are delayed coker naphtha, pyrolysis naphtha and ebulating bed naphtha. Such a mixture may also comprise aromatics, paraffins and naphthenic. The mixture of hydrocarbons may also comprise or is a fraction isolated from the effluent of a steam cracker process.

Instead or in addition to the above described olefinic feed the process according to this invention may also convert a more paraffinic and/or naphthenic mixture of hydrocarbons to propylene. Such a hydrocarbon feed comprises paraffins, naphthenics, aromatics and optionally up to 10 wt. % of olefins. Preferably such an additional or alternative feed boils for more than 90 vol. % between 35 and 280° C. and preferably between 35 and 240° C. When used as an additional feed the feed is preferably fed directly to the fixed bed reactor of step (c) together with the first high boiling fraction optionally in admixture with a recycle stream. When used as an alternative feed it is preferred to use this feed in step (a).

Such a more paraffinic and/or naphthenic mixture of hydrocarbons suitable has an olefin content of less than 10 wt. %, more preferably less than 5 wt. % and even more preferably less than 1 wt. % olefins. Examples of such mixtures are the refinery naphtha fractions such as straight run naphtha and light straight run naphtha or as obtained in a refinery hydroprocessing process, such as a hydrocracker or a hydrotreater process, also referred to as hydrotreated naphthas and hydrocracker naphthas. Other examples are polymerisation naphthas and reformer naphthas and natural gas liquids.

The conversion of olefins in step (a) is an endothermic reaction. The required energy may be added to the reactor in various manners. One preferred method is to add inert hydrocarbons, such as paraffins, naphthenic and/or aromatics, to the olefinic mixture. The thermal capacity of the feed will then increase per olefin mass. This is advantageously achieved by recycling part of the first high boiling fraction as obtained in step (b) to step (a). The weight fraction of the mixture of hydrocarbons having an olefin content of between 5 and 50 wt. % and boiling for more than 90 vol. % between 35 and 280° C., preferably between 35 and 240° C., in the total feed to the fixed bed reactor may therefore be between 25 and 75 wt. %.

Applicants have found that the presence of aromatics in the mixture as fed to the reactor in step (a) and to step (c) feed increases the cycle length, stabilizes activity and helps to maximize conversion. This effect is most profound when the feed to the reactor has a low content of olefins as when starting from the above described more paraffinic and/or naphthenic mixture of hydrocarbons as feed. When starting from the olefinic feed it may then be more preferred to have aromatics in the feed of step (c). The presence of aromatics does not affect selectivities substantially. Without wishing to be bound by the following theory it is believed that the presence of aromatics reduce the coke formation on the cracking catalyst by competitive adsorption on the catalyst surface or via dilution of coke precursors. Secondly the presence of the, substantially inert, aromatics may increase the conversion in fixed bed reactors by supplying heat to the endothermic cracking. The aromatics are preferably the aromatics boiling substantially in the same range or just above as the olefinic mixture of hydrocarbons. Examples of suitable aromatics are benzene, toluene, xylene, ethylbenzene and other aromatics having 8 or more carbon atoms, preferably up to and including 11 carbon atoms.

The aromatics may be present in the above described olefinic or paraffinic/naphthenic feeds as used in steps (a) and (c) of this process or may be present in the described recycle streams. Preferably aromatics are purposely added to the process mentioned above. For the olefinic feed to the fixed bed reactor in step (a) preferably at least 30 wt. % aromatics are present, more preferred 35 wt. %, more preferred 40 wt. % and even more preferred 50 wt. % aromatics. The optimum in aromatics content can be determined by the skilled person wherein the maximum conversion in a single pass may be a determining factor. The upper limit of aromatic content may be 80 wt. % while more preferred the content of aromatic compounds in the hydrocarbon mixture including optional recycle stream or streams as fed to the reactor in step (a) is between 40 and 50 wt. %.

For the mixture as provided to the fixed bed in step (c) it is preferred that it contains at least 5 wt. %, more preferably at least 10 wt. % of aromatics are present and even more preferred at least 20 wt. % and preferably at most 80 wt. %, more preferably at most 40 wt %. Such aromatic contents are especially preferred when the olefin conversion in step (a) is such that the olefin content in the first high boiling fraction obtained in step (b) has an olefin content of below 10 wt. % and more preferably below 5 wt. %. Such olefin contents are also preferred to operate step (c) at the desired cycle lengths and selectivity when the aromatics content is outside the above ranges.

As described above it is preferred to purposely add aromatics to the feed to the reactors in step (a) and (c). These aromatics may be sourced from other parts of for example a refinery or steam cracker. Preferably the aromatics are prepared in a separate processing step by contacting part of the first high boiling fraction and/or all or part of the second high boiling fraction in a step (f) with hydrogen in the presence of an aromatic conversion catalyst as present in a fixed bed to obtain a fraction rich in aromatics. By recycling all or part of the fraction rich in aromatics to step (a) and/or to step (c) the desired aromatic content may be achieved. Part of the fraction rich in aromatics may also be recycled to step (f) itself. Preferably part of the aromatics are isolated from these recycle streams to avoid a build up of the substantially inert aromatics. This in itself is not disadvantageous because these aromatics, such as benzene, toluene and xylene represent desirable compounds to be used as such.

Such an aromatics conversion step (f) is in itself known and also referred to as reforming. Step (f) may be performed using the well-known reforming processes as provided by UOP. Step (f) may take place at a temperature of between 400 and 550° C., at a weight hourly space velocity (WHSV) of between 0.5 and 5 $h^{-1}$, a hydrocarbon partial pressure below 10 bar and a hydrogen partial pressure below 10 bars.

The aromatic conversion catalyst may be any reforming catalyst or a heterogenous catalyst comprising ZnO, a medium pore zeolite and a binder. The medium pore zeolite is suitably ZSM-5 and the binder is suitably alumina. Suitably the binder comprises some $P_2O_5$. A preferred catalyst comprises between 25-60 wt. % ZSM-5, between 5 and 35 wt. % ZnO and between 2.5 and 20 wt. % $P_2O_5$ and an alumina binder. Such a catalyst may be prepared by adding a ZSM-5 zeolite, for example 50 parts of ZSM-5 crystal (SAR 30, ex Zeolyst), to a quantity of water. This aqueous mixture may be added to a gelled alumina, for example 35 parts dry base, Catapal B, ex Sasol, and zinc nitrate, for example 10 parts dry base, technical grade ex Alpha Aesar, and kneaded. To this kneaded mass $P_2O_5$, for example 5 parts, may be added as diluted phosphoric acid. The mixture is extruded and dried, for example at 120° C. for 1 hour and calcined, for example for 1 hr at 600° C.

In step (b) and (d) propylene and optionally other low boiling compounds is isolated from the effluent of step (a) and step (c) respectively and a high boiling fractions remains. The other low boiling compounds may be for example ethane, ethylene, hydrogen, water, propane and butylenes. Such a separation may include distillation and/or flash separation. Because the selectivity of propylene on the total of propylene and propane is improved less propane is formed. This is advantageous because a less difficult propylene and propane separation will be required to obtain for example a polymer grade propylene. In this separation ethylene may be isolated from the low boiling compounds. The $C_4$ fraction including butane and butylene may be recovered as such or be recycled together as part of the high boiling compounds as described.

The catalyst as present in the fixed bed of the fixed bed reactor in step (a) may be any cracking catalyst which has a relatively low acidic density. The low acidic density has a relatively large distance between the acid sites which avoids that reaction intermediate compounds can form coke. The catalyst is active in the conversion of olefins while paraffins almost not react. A possible low acidic density catalyst is an amorphous catalyst, such as for example a catalyst comprising amorphous silica alumina, silica zirconia and/or silica borate as the amorphous low acidic density component. Preferably the low acidic density catalyst in step (a) is a heterogenous catalyst comprising a medium or large pore zeolite having a silica to alumina ratio of between 2 and 1000, more preferred between 10 and 1000, even more preferred between 10 and 300, even better preferred between 20 and 300 and most preferred between 20 and 100. For example one may start with a fresh catalyst having a relatively low silica to alumina ratio. In time this ratio may increase to a higher ratio due to dealumination. The resulting decrease in activity may be compensated by operating at a higher temperature. Examples of suitable medium or large pore zeolites are ZSM-5, ZSM-11 and Beta zeolite. An example of a suitable low acidic density catalyst comprises up to 70 wt. % ZSM 5, between 1-20 wt. % $P_2O_5$ and a binder. Examples of suitable binders are alumina, such as boehmite, optionally in admixture with a clay to increase strength. The catalyst preferably comprises between 25 and 80 wt %, more preferred between 25 and 70 wt % and even more preferred between 35 and 50 wt. % ZSM-5.

The catalyst as present in the fixed bed of the fixed bed reactor in step (c) may be any cracking catalyst which has a relatively high acidic density. When the first high boiling fraction contains high contents of olefins, especially in case the content of olefins is higher than the contents of olefins in the mixture of hydrocarbons as fed to step (a) a lower acidic density catalyst may also be used, for example such as the catalyst described above for step (a). The high and low acidic density catalysts may therefore preferably comprise a large pore or medium pore zeolite having a relatively low silica to alumina ratio. Preferably the silica to alumina ratio of the high acidic density catalyst is lower than the silica alumina ratio of the low acidic density catalyst. Examples of suitable medium or large pore zeolites are ZSM-5, ZSM-11 and Beta zeolite. An example of a suitable the high acidic density catalyst in step (c) is a heterogenous catalyst comprising up to 80 wt %, preferably up to 70 wt. % ZSM 5 having a silica to alumina ratio of between 2 and 1000, more preferred between 10 and 1000, even more preferred between 10 and 300, even better preferred between 25 and 100, between 1-20 wt. % $P_2O_5$ and a binder. Examples of suitable binders are alumina, such as boehmite, optionally in admixture with a clay to increase strength. The catalyst preferably comprises between 25 and 80 wt %, more preferred between 25 and 70 wt % and even more preferred between 35 and 50 wt. % ZSM-5.

The catalysts in step (a) and/or in step (c) may be steamed prior to use. This is to cause some initial deactivation of the catalyst to limit the activity range. With a more limited activity range conversion can be controlled by adjusting temperature. This is not possible if the activity range is too large. Steaming may be performed by contacting the catalyst in the fixed bed with a gas comprising of 5-100 vol. % steam, preferably 10-100 vol. % steam, more preferably between 50-100 vol. % and even more preferably between 70-95 vol. %. The preferred pressure may be between about atmospheric pressure with a maximum pressure of 10 bar. The preferred temperature is between 600 and 800° C. and more preferred between 725 and 775° C. The contacting time may be from 1 hour to 5 days wherein contact times of about 1 day is preferred.

Equilibrated catalysts of step (c) which have to be replaced due to their higher silica alumina ratio may be advantageously used as the catalyst in step (a).

The zeolite comprising catalysts used in steps (a) and (c) may be prepared starting from a zeolite having the desired silica to alumina ratio. The zeolite is suitably slurried in distilled water and mixed with an alumina gel. The gel is for example prepared by using nitric acid and Catapal B from Sasol. The mixture is extruded yielding a particle comprising a zeolite and an alumina binder. The particle is calcined, for example in air for 1 hour at 600° C. The calcined particle is subsequently impregnated with phosphoric acid and calcined again, for example in air for 1 hour at 600° C.

In the process according to this invention the weight hourly space velocity is defined on the total of hydrocarbons fed to a fixed bed reactor. Thus also including optional recycle streams and/or added rich aromatic streams. This also applies to the temperature of the feed to the reactors. The temperature values refer to the temperature of the total of hydrocarbons fed to the fixed bed reactor.

Preferably the weight hourly space velocity in step (a) is between 0.5 and 100 $h^{-1}$, more preferred between 1 and 100 $h^{-1}$, even more preferred between 10 and 50 $h^{-1}$ and most preferred between 5 and 50 $h^{-1}$. Between 15 and 30 $h^{-1}$ is further preferred. The weight hourly space velocity in step (c) is between 0.5 and 100 $h^{-1}$, more preferred between 1 and 100 $h^{-1}$, even more preferred between 2 and 50 $h^{-1}$ and most preferred between 5 and 30 $h^{-1}$ or between 5 and 20 $h^{-1}$. Preferably the weight hourly space velocity in step (a) is greater than the weight hourly space velocity in step (c). The hydrocarbon partial pressure is preferably below 1 bar, more preferred below 0.5 bar and even more preferred below 0.2 bar.

The temperature of the mixture of hydrocarbons optionally in admixture with a recycle stream to step (a) has a temperature between 400 and 750° C., preferably between 450 and 700° C., more preferred between 450-650° C. and most preferred between 500 and 600° C.

The temperature of the first high boiling fraction optionally in admixture with a recycle stream in step (c) is between 400 and 750° C., preferably between 450 and 700° C., more preferably between 450 and 650° C. and most preferably between 500 and 600° C.

The fixed bed reactor in step (a), in step (c) and/or in step (f) is preferably a configuration of more than one reactor. For example such a configuration may be a set of parallel operated reactors or for example a so-called simulated moving bed configuration.

As described above, applicant found that the presence of aromatics is advantageous to achieve high cycle lengths, stabilizes activity and helps to maximize conversion for paraffinic/naphthenic mixtures. For this reason the invention is also directed to the following processes.

Process to prepare propylene from a hydrocarbon starting feed comprising paraffins, naphthenics, aromatics and optionally up to 10 wt. % of olefins by adding aromatic compounds to the hydrocarbon starting feed resulting in an upgraded feed containing between 10 and 70 wt %, preferably between 20 and 50 wt % and even more preferably between 25 and 40 wt % aromatic compounds, wherein the content of aromatics in the starting feed is below the lower end of these ranges and wherein the upgraded feed is catalytically cracked in the presence of an acidic cracking catalyst to propylene and other reaction products.

The aromatic compounds added to the hydrocarbon starting feed may be any aromatic compound including aromatic compounds boiling in the gas oil boiling range. Suitably the aromatics as described above are added to the hydrocarbon starting feed. The acidic cracking catalyst may be as described in this application. The reactor and conditions may be those as described for this invention. Alternatively the reactor may be a fluidized bed. The aromatics added to the hydrocarbon starting feed may be aromatics as separated from the reaction products of this process which are reused in the process. It appears that the aromatics are not cracked in any significant level to other products and that the amount of total aromatics in the upgraded feed and the reactor effluent is about the same.

Such a recycle process is described in the following process according to the invention. Process to prepare propylene from a hydrocarbon feed comprising paraffins, naphthenics, aromatics and optionally up to 10 wt. % of olefins wherein the process comprises the following steps:

(aa) feeding the feed in admixture with a recycle stream and having a temperature of between 450 and 700° C., preferably between 550 and 700° C., to a continuously operated fixed bed reactor comprising a high acidic density cracking catalyst where the mixture is contacted with a high acidic density cracking catalyst at a hydrocarbon partial pressure of below 3 bar and at a weight hourly space velocity of between 1 and 30 h$^{-1}$, preferably between 2 and 30 h-1, (bb) isolating propylene and optionally other low boiling compounds from the effluent of step (aa) wherein a high boiling fractions remains, (cc) recycling part of the high boiling fraction to the fixed bed reactor of step (aa) wherein the total content of aromatics in the combined mixture as fed to the fixed bed reactor in step (aa) is maintained at between 10 and 40 wt. %, optionally by additionally feeding an aromatic comprising further hydrocarbon mixture to the fixed bed reactor.

The high acidic density catalyst in step (aa) may be as described earlier for step (c). The preferred conditions and catalyst for operating this process are the same as described above for steps (c) to (e) as described above. It is also preferred to add an aromatics conversion which uses the high boiling fraction in a step (dd) with hydrogen in the presence of an aromatic conversion catalyst as present in a fixed bed to obtain a fraction rich in aromatics and wherein all or part of the fraction rich in aromatics is recycled to step (aa) as the further hydrocarbon mixture. The conditions and catalyst are those described above.

The feed for this process may boil for more than 90 vol. % between 35 and 280° C. and preferably for more than 90 vol. % between 35 and 240° C. The feed suitably has an olefin content of less than 10 wt. %, more preferably less than 5 wt. % and even more preferably no olefins. Examples of such mixtures are the naphtha fractions as obtained in a refinery hydroprocessing process, such as a hydrocracker or a hydrotreater process.

The invention is also directed to a process configuration suited to prepare propylene from an olefin comprising hydrocarbon mixture comprising (i) one or more parallel operated first fixed bed reactors comprising an amorphous heterogeneous cracking catalyst or a heterogeneous cracking catalyst comprising a medium or large pore zeolite having a silica to alumina ratio of between 1 and 1000, (ii) first distillation and/or flash separation units fluidly connected to the outlet of the one or more first fixed bed reactors having at least an outlet for a propylene comprising fraction and an outlet for high boiling compounds, (iii) means to recycle the high boiling compounds from the outlet of the distillation and/or flash separation units to the inlet of the one or more first fixed bed reactors, (iv) one or more parallel operated second fixed bed reactors comprising a heterogeneous cracking catalyst comprising up to 80 wt. % ZSM-5 having a silica to alumina ratio of between 2 and 1000, preferably between 25 and 50, between 1-20 wt. % $P_2O_5$ and a binder and wherein the inlet of the fixed bed reactors are fluidly connected to the outlet for high boiling compounds of the first distillation and/or flash separation unit, (v) second distillation and/or flash separation units fluidly connected to the outlet of the one or more second fixed bed reactors of (iv) having at least an outlet for a propylene comprising fraction and an outlet for high boiling compounds, (vi) means to recycle the high boiling compounds from the outlet of the second distillation and/or flash separation units to the inlet of the one or more first fixed bed reactors and to the inlet of the one or more second fixed bed reactors.

Preferably the process configuration further comprising inlet means (vii) for a further hydrocarbon feed fluidly connected to the inlet of the one or more parallel second fixed bed reactors. Flash separation units may be suitably combined with a stripping step to recover any $C_5$ plus compounds which may be present in the gaseous effluent.

Preferably the process configuration further comprises (viii) one or more parallel operated aromatic conversion fixed bed reactors fluidly connected to the outlet for high boiling compounds of the second distillation and/or flash separation units and means to recycle part of the effluent of the aromatic conversion fixed bed reactors to the inlet of the one or more first fixed bed reactors, to the inlet of the one or more second fixed bed reactors and to the inlet of the aromatics conversion fixed bed reactors. The aromatic conversion fixed bed reactors suitably have an inlet for hydrogen and have a bed of a heterogeneous catalyst comprising ZnO, a medium pore zeolite and a binder as also described above.

The one step process or step (c) of the two step process according to this invention is an energy intensive process which may yield high amounts of light olefins, like ethylene, propylene and butylene. The hydrocarbon feed may be heated to a reactor inlet temperature of 450° C. or greater via a feed/effluent heat exchanger followed by a natural gas fired heater. The reactor effluent may then further be reduced in temperature by a combination of an air-cooled heat exchanger and a chilled water heat exchanger with the target temperature being suitably between 25-30° C. The low boiling fraction may then be separated via a single stage equilibrium flash wherein the overhead vapors as the low boiling products are further separated in a product recovery unit. The high boiling and non-reacted liquid hydrocarbon may be advantageously be recycled. This recycle having a temperature of for example between 25-30° C. is combined with fresh hydrocarbon feed and reheated to reactor inlet temperatures of 450° C. or greater.

A less energy intensive alternative process modifies the basic process described above as follows. The reactor effluent exchanges heat with the feed in a feed/effluent heat exchange network and is subsequently fed to a distillation column, such as a debutanizer distillation column. The operating temperature of the reactor effluent exiting the feed/effluent heat exchange may range between 200-300° C. The butylene and lighter components of the reactor effluent are taken overhead from the distillation column as the low boiling compounds. The pentane and heavier components of the reactor effluent are the bottoms product from the distillation column, ie the high boiling compounds. The bottoms product is treated as recycle as described in the base configuration above. The operating temperature of the recycle stream exiting the debutanizer distillation column bottoms stream may have a temperature of 250-350° C. A preferred recycle-to-fresh feed ratio varies between 2.0-4.0 (recycle mass rate/fresh feed mass right). For example 67 wt % of the reactor feed consists of recycle. The alternative process described above eliminates the need to impart up to 420° C. energy equivalent into the reactor feed for this recycle stream resulting in significant energy savings. A negative consequence of the alternative process flow scheme is the debutanizer distillation column pressure drop which may be 3.0 psig. This is higher than the pressure drop of approximately 2.0 psig resulting from cooling the reactor effluent in air cooled followed by water cooled heat exchangers. This additional 1.0 psig pressure drop may be added to the reactor inlet operating pressure when using the alternative process.

Because increasing the inlet pressure of the reactor may negatively influence the propylene selectivity it is preferred that the debutanizer distillation column is operated under partial vacuum in order to eliminate the required reactor inlet pressure increase. The debutanizer distillation column overhead accumulator drum will operate as the section drum for a centrifugal compressor. The centrifugal compressor may preferably produce an overall vacuum of approximately 10-15 psia. This will eliminate the need to increase reactor inlet pressure while gaining the benefit of the alternate process flow. The reactor inlet pressure of the alternate process may for example operate with a reactor inlet pressure of 18.5 psia versus 37.1 psia for the base process resulting in a further increase in propylene selectivity.

The centrifugal compressor discharge may pass through a chilled water heat exchanger to reduce the operating temperature to approximately 30° C. The cooled hydrocarbon stream will be routed to a high-pressure separator for the efficient removal of higher molecular weight compounds. The overhead vapor stream from this separator will be routed to a second boost centrifugal compressor in order to impart pressure for product separations. The high-pressure separator liquid hydrocarbon stream may then be distilled in the product recovery section with a lower energy requirement as a result of operating at the higher pressure.

EXAMPLE 1

To a pilot plant reactor containing 1.5 grams of a fixed bed catalyst at a WHSV of 30 $h^{-1}$ a FCC naphtha boiling between 20 and 206° C. and having the composition as listed in Table 1 was fed. The temperature in the reactor was 600° C.

ZSM-5 crystal with SAR 30 (CBV 3024E, ex Zeolyst) was mulled in a 55/45 wt/wt. mixture with alumina (ex Sasol) and extruded to prepare a formed mass. The extruded mass was dried at 120° C. overnight and calcined for 3 hours in flowing air at 600° C. The calcined extrudates were impregnated to incipient wetness with phosphoric acid and then dried at 120° C. overnight and calcined for 3 hours at 600° C. in flowing air.

TABLE 1

| | | |
|---|---|---|
| Total Normal Paraffin | 4.4 | % wt |
| Total Iso Paraffin | 31.1 | % wt |
| Total Saturated Naphthene | 6.9 | % wt |
| Total Unsaturated Naphthene | 3.9 | % wt |
| Total Normal Olefin | 12.3 | % wt |
| Total Iso Olefin | 19.8 | % wt |
| Total Di Olefin | 0.2 | % wt |
| Total Aromatic | 21.4 | % wt |
| Total | 100.0 | % wt |

The composition of the reaction products are listed in Table 2.

EXAMPLE 2

Example 1 was repeated except that 20 wt % of the feed was replaced by toluene. This resulted in that the total conversion (defined as: (the mass production of H2, C1-C4 hydrocarbons and delta aromatics)/(mass feedstock)*100%) dropped from 22 wt % to 19 wt % and the conversion of the FCC naphtha itself increased from 22 wt % to 24 wt %. The addition of toluene illustrates the advantageous effect of a recycle containing aromatics to the cracking reactor. In Example 1 the conversion for the feed as is was 22%. In Example 2 the conversion was the absolute conversion on total feed basis was 19%, or 24% conversion on the FCC naphtha part of the feed. Product selectivities were not affected by the addition of the aromatics, as is shown by the results reported in table 2.

TABLE 2

| Reaction products (wt % of the C1-C4 fraction + delta aromatics) | Example 1 Feed FCC naphtha | Example 2 Feed FCC naphtha plus 20 wt % toluene |
|---|---|---|
| CH4 | 1% | 1% |
| C2+ | 1% | 1% |
| C2= | 16% | 16% |
| C3+ | 4% | 3% |
| C3= | 42% | 43% |
| iC4+ | 1% | 1% |
| nC4+ | 1% | 1% |
| iC4= | 9% | 9% |
| nC4= | 15% | 15% |
| aromatics | 10% | 10% |
| Total Coke yield | 0.13 wt % | 0.08 wt % |

EXAMPLE 3

Example 1 was repeated for about 3000 minutes (50 hours) except that the feed is now hexane and the WHSV was 60 h$^{-1}$. The conversion of the feed in time is presented by the black circles (w/o aromatics) in FIG. 1.

EXAMPLE 4

Figure 1:
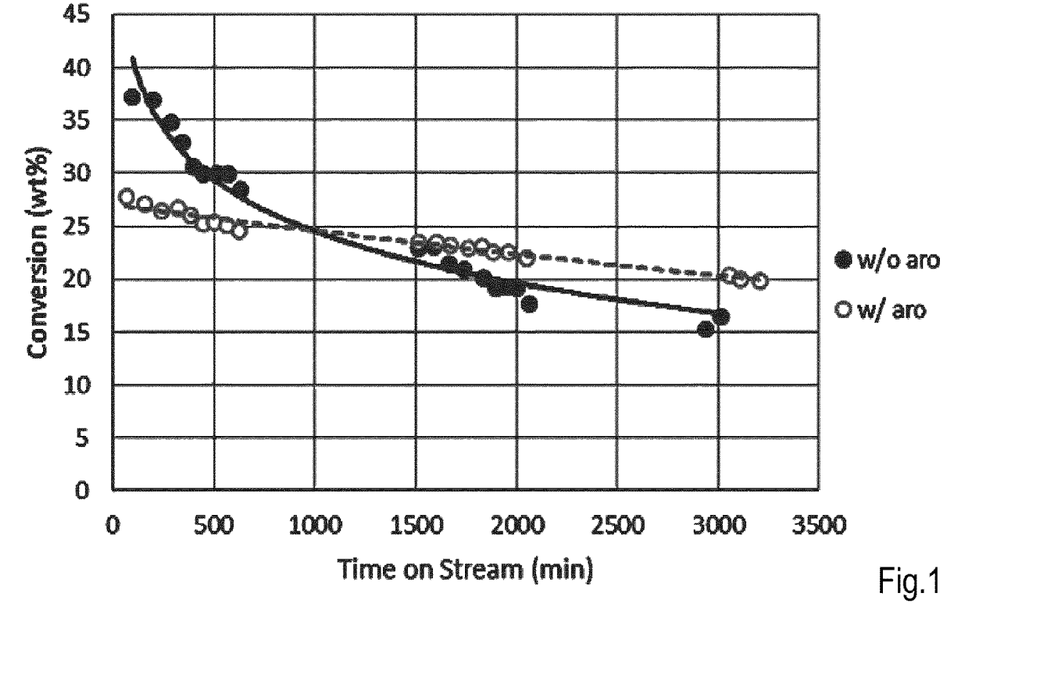

Example 3 was repeated except that 20 wt % of the feed was replaced by toluene. The conversion of the feed in time is presented by the open circles (w/aro) in FIG. 1. In FIG. 1 it is shown that the conversion of the crackable part of the feed (hexanes) was initially lower when toluene was added. Example 4 with toluene showed substantially improved stability and the catalyst deactivation with time on stream due to coking of the catalyst was significantly reduced. The addition of toluene did not negatively affect product selectivities of propylene (for both experiments around 35%) and butylenes (for both experiments around 20-24%).

EXAMPLE 5

To a pilot plant reactor containing 3 grams of a fixed bed catalyst described in example 1 at a WHSV of 10 h$^{-1}$ a non-olefinic feed having the composition as listed in Table 3 and boiling between 20 and 220° C. was fed during about 1200 minutes. The temperature in the reactor was 600° C. The conversion in time is shown as the black circles (1st pass) in FIG. 2.

TABLE 3

| compounds | Wt % |
| --- | --- |
| Total Normal Paraffins | 23 |
| Total Iso Paraffins | 44 |
| Total Naphthenes | 23 |
| Total Olefins | 0 |
| Total Aromatics | 10 |
| Xylenes | 3.3 |
| C9 aromatics | 6.7 |
| Total | 100 |

EXAMPLE 6

Example 5 was repeated wherein part of the reactor liquid effluent was recycled to the reactor thereby substituting part of the feed such that the feed now consisted of 80 wt % recycle and 20 wt % fresh feed. The recycle contained 2 wt % olefins. The conversion in time is shown as the open circles (recycle) in FIG. 2.

Figure 2:
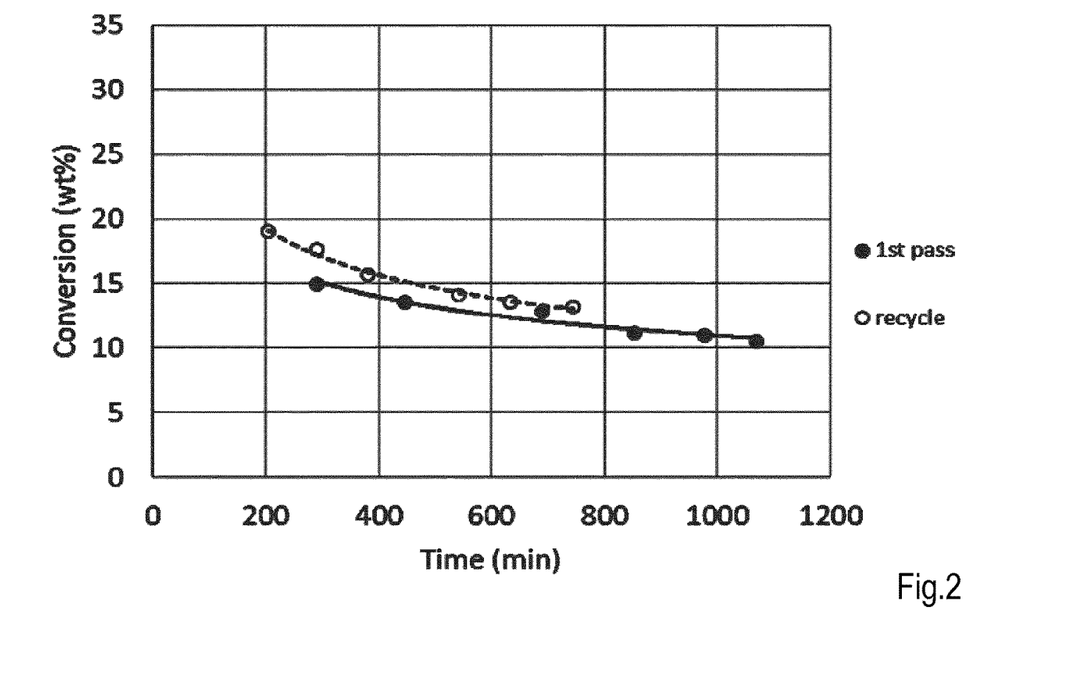

FIG. 2 shows that the total conversion (of total combined feed to the reactor) is higher when part of the liquid effluent is recycled to the reactor. The selectivities to the desired C3 and C4 olefins were not influenced in any significant manner when examples 5 and 6 were compared.

The invention claimed is:

1. A process to prepare propylene from a mixture of hydrocarbons having an olefin content of between 5 and 50 wt. % and boiling for more than 90 vol. % between 35 and 280° C. or from a hydrocarbon feed comprising paraffins, naphthenics, aromatics and optionally up to 10 wt. % of olefins, wherein the process comprises the following steps:
   (a) feeding a feedstock having a temperature between 450 and 750° C. and optionally in admixture with a recycle stream to a fixed bed reactor where the feedstock comprises the mixture of hydrocarbons and/or the hydrocarbon feed and is contacted with a low acidic density cracking catalyst comprising a large or medium pore zeolite having a silica alumina ratio at a hydrocarbon partial pressure of below 3 bar and at a weight hourly space velocity of between 0.5 and 100 h$^{-1}$,
   (b) isolating propylene and optionally other low boiling compounds having a boiling point lower than or equal to that of C4 hydrocarbons from an effluent of step (a) wherein a first high boiling fraction having a boiling point of higher or equal to that of C4 hydrocarbons remains,
   (c) feeding all or a part of the first high boiling fraction having a temperature between 400 and 750° C. and optionally in admixture with a recycle stream to a fixed bed reactor where the all or part of the first high boiling fraction is contacted with a high acidic density cracking catalyst comprising a large or medium pore zeolite having a silica alumina ratio which is lower than the silica alumina ratio of the low acidic density cracking catalyst at a hydrocarbon partial pressure of below 3 bar and at a weight hourly space velocity of between 0.5 and 100 h$^{-1}$ and wherein the temperature of feedstock as fed to the fixed bed reactor in step (a) is lower than the temperature of the all of part of the first high boiling fraction optionally in admixture with a recycle stream as fed to the reactor in step (c),
   (d) isolating propylene and optionally other low boiling compounds from an effluent of step (c) wherein a second high boiling fractions remains, and
   (e) recycling all or a part of the second high boiling fraction to step (a) and/or to step (c) as the recycle stream of step (a) and/or step (b).

2. The process according to claim 1, wherein the weight hourly space velocity in step (a) is greater than the weight hourly space velocity in step (c).

3. The process according to claim 1, wherein a part of the first high boiling fraction and/or all or a part of the second high boiling fraction is contacted in a step (f) with hydrogen in the presence of an aromatic conversion catalyst as present in a fixed bed to obtain a fraction rich in aromatics and wherein all or a part of the fraction rich in aromatics is recycled to step (c) as an optional recycle stream and/or to step (f).

4. The process according to claim 3, wherein contacting in step (f) takes place at a temperature of between 400 and 550° C., at a weight hourly space velocity of between 0.5 and 5 h$^{-1}$, a hydrocarbon partial pressure below 10 bar and a hydrogen partial pressure below 10 bars.

5. The process according to claim 3, wherein the aromatic conversion catalyst is a heterogenous catalyst comprising ZnO, a medium pore zeolite and a binder.

6. The process according to claim 1, wherein the low acidic density cracking catalyst in step (a) is a heterogenous catalyst comprising a medium or large pore zeolite having a silica to alumina ratio of between 2 and 1000.

7. The process according to claim 6, wherein the heterogenous catalyst comprises up to 70 wt. % ZSM-5, between 1-20 wt. % P$_2$O$_5$ and a binder.

8. The process according to claim 6, wherein the heterogenous catalyst comprises between 25 and 80 wt. % ZSM-5.

9. The process according to claim 1, wherein the weight hourly space velocity in step (a) is between 0.5 and 100 h$^{-1}$.

10. The process according to claim 1, wherein the high acidic density cracking catalyst in step (c) is a heterogenous catalyst comprising up to 80 wt. % ZSM-5 having a silica to alumina ratio of between 2 and 1000, between 1-20 wt. % P$_2$O$_5$ and a binder.

11. The process according to claim 1, wherein the low acidic density cracking catalyst and/or the high acidic density cracking catalyst is a heterogenous catalyst comprising between 35 and 50 wt. % ZSM-5.

12. The process according to claim 1, wherein the weight hourly space velocity in step (c) is between 0.5 and 100 h$^{-1}$.

13. The process according to claim 1, wherein the mixture of hydrocarbons comprises a fraction as isolated from an effluent of a Fluid Catalytic Cracking process and/or isolated from an effluent of a steam cracker process.

14. The process according to claim 1, wherein the content of aromatic compounds in the combined hydrocarbons as fed to the fixed bed reactor in step (c) is between 10 and 80 wt. %.

15. The process according to claim 1, wherein a part of the second high boiling fraction as obtained in step (d) is recycled to step (c) as the recycle stream.

16. The process according to 15, wherein in step (d) propylene and other low boiling compounds are isolated from the effluent of step (c) in a debutanizer distillation column which is operated under partial vacuum and wherein the second high boiling fraction is obtained as a bottom product of the debutanizer distillation column.

17. A process to prepare propylene from a hydrocarbon feed comprising paraffins, naphthenics, aromatics and optionally up to 10 wt. % of olefins wherein the process comprises the following steps:
(aa) feeding the hydrocarbon feed in admixture with a recycle stream and having a temperature of between 450 and 700° C. to a continuously operated fixed bed reactor comprising a heterogenous cracking catalyst comprising up to 80 wt. % ZSM-5 having a silica to alumina ratio of between 2 and 1000, between 1-20 wt. % $P_2O_5$ and a binder where the admixture is contacted with the heterogenous cracking catalyst at a hydrocarbon partial pressure of below 3 bar and at a weight hourly space velocity of between 1 and 30 h$^{-1}$,
(bb) isolating propylene and optionally other low boiling compounds having a boiling point lower than or equal to that of C4 hydrocarbons from an effluent of step (aa) wherein a high boiling fraction having a boiling of higher or equal to that of C4 hydrocarbons remains,
(cc) recycling a part of the high boiling fraction to the fixed bed reactor of step (aa) wherein the total content of aromatics in the combined mixture hydrocarbons as fed to the fixed bed reactor in step (aa) is maintained at between 10 and 40 wt. %, optionally by additionally feeding an aromatic comprising further hydrocarbon mixture to the fixed bed reactor.

18. The process according to 17, wherein in step (bb) propylene and other low boiling compounds are isolated from the effluent of step (aa) in a distillation column which is operated under partial vacuum and wherein the high boiling fraction is obtained as a bottom product of the distillation column.

19. The process according to claim 17, wherein a part of the high boiling fraction is contacted in a step (dd) with hydrogen in the presence of an aromatic conversion catalyst as present in a fixed bed to obtain a fraction rich in aromatics and wherein all or a part of the fraction rich in aromatics is recycled to step (aa) as the further hydrocarbon mixture.

20. The process according to claim 19, wherein contacting in step (dd) takes place at a temperature of between 400 and 550° C., at a weight hourly space velocity of between 0.5 and 5 h–1, a hydrocarbon partial pressure below 10 bar and a hydrogen partial pressure below 10 bars.

21. The process according to claim 19, wherein the aromatic conversion catalyst is a heterogenous catalyst comprising ZnO, a medium pore zeolite and a binder.

22. A process system suited to prepare propylene from an olefin comprising hydrocarbon mixture, the system comprising
(i) one or more parallel operated first fixed bed reactors comprising an amorphous heterogeneous cracking catalyst or a heterogeneous cracking catalyst comprising a medium or large pore zeolite having a silica to alumina ratio of between 1 and 1000,
(ii) first distillation and/or flash separation units fluidly connected to an outlet of the one or more parallel operated first fixed bed reactors, said first distillation and/or flash separation units having at least an outlet for a propylene comprising fraction and an outlet for high boiling compounds having a boiling point of higher or equal to that of C4 hydrocarbons,
(iii) means to recycle the high boiling compounds from the outlet of the first distillation and/or flash separation units to an inlet of the one or more parallel operated first fixed bed reactors,
(iv) one or more parallel operated second fixed bed reactors comprising a heterogeneous cracking catalyst comprising up to 80 wt. % ZSM-5 having a silica to alumina ratio of between 2 and 1000, between 1-20 wt. % $P_2O_5$ and a binder, wherein an inlet of the one or more parallel operated second fixed bed reactors is fluidly connected to the outlet for high boiling compounds of the first distillation and/or flash separation unit, wherein the heterogeneous cracking catalyst in the one or more second fixed reactors has a silica alumina ratio which is lower than that of the amorphous heterogeneous cracking catalyst or the heterogenous cracking comprising a medium or large pore zeolite in the one or more first fixed bed reactors, and the one or more first fixed bed reactors are configured to operate at a lower temperature than the one or more second fixed bed reactors,
(v) second distillation and/or flash separation units fluidly connected to an outlet of the one or more parallel operated second fixed bed reactors of (iv), said second distillation and/or flash separation units having at least an outlet for a propylene comprising fraction and an outlet for high boiling compounds having a boiling point of higher than or equal to that of C4 hydrocarbons, and
(vi) means to recycle the high boiling compounds from the outlet of the second distillation and/or flash separation units to the inlet of the one or more first fixed bed reactors and to the inlet of the one or more second fixed bed reactors.

23. The system according to claim 22, further comprising inlet means (vii) for a further hydrocarbon feed fluidly connected to the inlet of the one or more parallel second fixed bed reactors.

24. The system according to claim 22, further comprising (viii) one or more parallel operated aromatic conversion fixed bed reactors fluidly connected to an outlet for high boiling compounds of the second distillation and/or flash separation units and means to recycle a part of an effluent of the aromatic conversion fixed bed reactors to the inlet of the one or more parallel operated first fixed bed reactors, to the inlet of the one or more parallel operated second fixed bed reactors and to an inlet of the one or more parallel operated aromatics conversion fixed bed reactors.

25. The system according to claim 24, wherein the one or more parallel operated aromatic conversion fixed bed reactors have an inlet for hydrogen and have a bed of a heterogeneous catalyst comprising ZnO, a medium pore zeolite and a binder.

* * * * *